United States Patent [19]

Limbert et al.

[11] Patent Number: 4,919,932
[45] Date of Patent: Apr. 24, 1990

[54] PHARMACEUTICAL FORMULATION FOR THE TREATMENT OF BACTERIAL INFECTIONS

[75] Inventors: Michael Limbert, Taunus; Elmar Schrinner, Wiesbaden; Gerhard Seibert, Darmstadt, all of Fed. Rep. of Germany

[73] Assignee: Hoechst Aktiengesellschaft, Frankfurt am Main, Fed. Rep. of Germany

[21] Appl. No.: 56,712

[22] Filed: Jun. 2, 1987

[30] Foreign Application Priority Data

Jun. 4, 1986 [DE] Fed. Rep. of Germany ....... 3618813

[51] Int. Cl.$^5$ ................... A61K 35/00; A61K 31/345; A61K 31/395
[52] U.S. Cl. .................... 424/114; 514/203; 514/206; 514/210
[58] Field of Search ....... 514/203, 206, 210; 424/114

[56] References Cited

U.S. PATENT DOCUMENTS 4,560,550 12/1985 Osborne ............... 424/114
4,585,767 4/1986 Cooke et al. ........... 514/210

FOREIGN PATENT DOCUMENTS 120613 3/1984 European Pat. Off. .
170026 5/1986 European Pat. Off. .
2017493 10/1979 United Kingdom .

OTHER PUBLICATIONS

Biological Abstracts, 72((223:217(1981).

Primary Examiner—Douglas W. Robinson
Attorney, Agent, or Firm—Finnegan, Henderson, Farabow, Garrett and Dunner

[57] ABSTRACT

A pharmaceutical formulation having a synergistic antibacterial activity and comprising
(a) a cephalosporin derivative or a physiologically acceptable salt or ester thereof and
(b) a penem antibiotic of the basic structure (B)

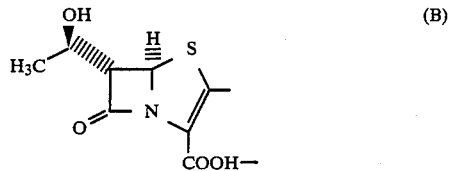

or a physiologically acceptable salt or ester thereof, a process for preparing such a formulation and its use for the treatment of bacterial infections.

2 Claims, No Drawings

PHARMACEUTICAL FORMULATION FOR THE TREATMENT OF BACTERIAL INFECTIONS

It is known that antibiotics from the class of cephalosporins, for example cefotaxim, cefodizim or cefpirom, are outstandingly suitable for the therapy of bacterial infections, but that the antibacterial activity towards certain Gram-positive and Gram-negative aerobic and especially anaerobic pathogens can be inadequate.

Antibiotics from the group of the penems, for example 5R,6S-6-(1R-hydroxyethyl)-3-(4-carbamoylphenoxy)-7-oxo-4-thia-1-azabicyclo[3.2.0]hept-2-ene-carboxylic acid known from EP-A No. 0,170,028 have an antibacterial activity which destroys many pathogenic organisms, towards which the cephalosporins have only a low activity.

EP-A-No. 0,120,613 has disclosed that synergistic activities between certain penems and penicillins or cephalosporins can arise. As compared with the penem/cephalosporin combinations described therein, the formulations according to the invention are distinguished by a substantially higher antibacterial activity.

It has now been found, surprisingly, that cephalosporins in combination with certain penems have a markedly synergistic antibacterial effect.

The invention therefore relates to pharmaceutical formulations having a synergistic antibacterial activity and comprising (a) a cephalosporin derivative or physiologically acceptable salts or esters thereof and
(b) a penem antibiotic of the basic structure (B)

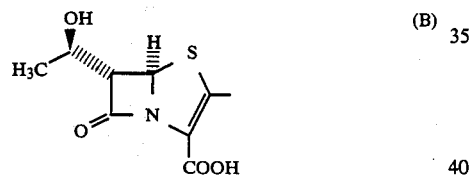

or physiologically acceptable salts or esters thereof.

Amongst the cephalosporin derivatives, aminothiazolecephalosporins and physiologically acceptable salts or esters thereof are preferred according to the invention, in particular those having the basic structure (A)

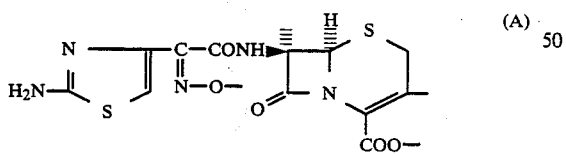

in which the =N—O— group is in the syn-position, such as are described, for example, in German Offenlegungsschriften Nos. 2,702,501, 2,713,272, 2,715,385, 2,810,922, 2,921,316 and 2.922,036, in EP-A No. 0,064,740, in U.S. Pat. Nos. 4,278,793 and 4,501,739 and in GB-A No. 2,105,334 and 2,105,335. However, other cephalosporins such as, for example, N-acyl-phenylglycine-cephalosporins or those in which the group —CH$_2$— takes the place of the —C(=N—O—)— group in the basic structure (A) can also be used according to the invention.

Penem antibiotics of the basic structure (B) are described, for example, in EP-A No. 0,069,377, EP-A No. 0,170,028, GB-A No. 85.20,631, EP-A No. 121,502, British Pat. No. 2,097,786 and Belgian Pat. No. 898,603.

Of the cephalosporin antibiotics of the basic structure (A), those of the general formula I are particularly preferred

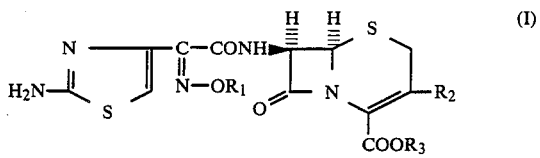

in which $R_1$ can be hydrogen, $C_1$–$C_4$-alkyl or carboxy-$C_1$–$C_4$-alkyl and the group =N—OR$_1$ is in the syn-position, $R_2$ can have the meaning of hydrogen, methyl, methoxy, vinyl, acetoxymethyl or carbamoyloxymethyl, of —CH$_2$S—X, with X=

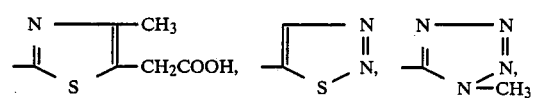

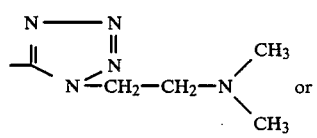

with Y=hydrogen, $C_1$–$C_4$-alkylthio, $C_1$–$C_4$-alkoxy or $C_3$–$C_5$-cycloalkyl,

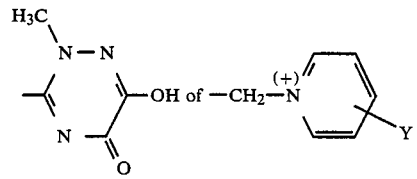

it being possible for the fused rings also to be in the 3,4-position and also to be interrupted by oxygen, of

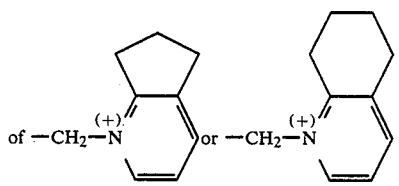

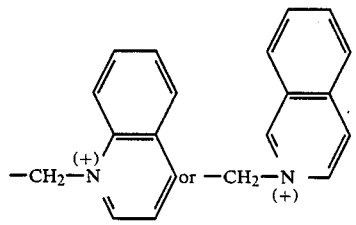

of thienopyridinio-methyl, furopyridinio-methyl or of 5-methyl-tetrazol-2-yl-methyl and $R_3$ is hydrogen, a physiologically acceptable cation, a physiologically acceptable ester radical or — if the structure

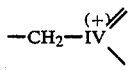

appears in $R_2$ — can represent a negative charge.

If $R_1$ is $C_1$–$C_4$-alkyl, examples are methyl, ethyl and propyl, preferably methyl.

If $R_1$ is carboxy-$C_1$–$C_4$-alkyl, carboxymethyl, carboxyethyl, carboxypropyl, preferably the radical —$CH_2$—COOH, but especially the radical

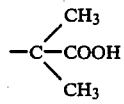

are examples of interest.

Amongst the substituted pyridinium-methyl radicals listed above, 2,3-cyclopenteno- and 2,3-cyclohexeno-pyridinium-methyl and 4-methylthio-, 4-cyclopropyl- and 3-methoxy-pyridinium-methyl as well as 3,4-cyclopenteno- and 3,4-cyclohexeno-pyridinium-methyl are preferred.

Those compounds of the formula I are of very particular interest according to the invention in which $R_1$ is methyl and $R_2$ is —$CH_2$—$OCOCH_3$ (cefotaxim),

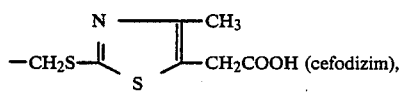

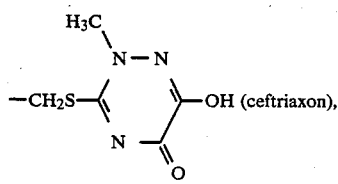

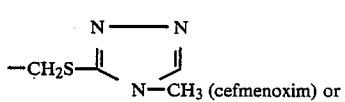

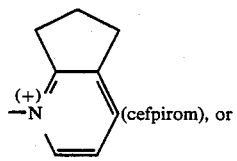

$R_1$ is —$CH_2COOH$ and $R_2$ is —CH=$CH_2$ (cefixim), cefodizim, cefpirom, ceftriaxon and especially cefotaxim in turn being in a preferred position within this group.

If $R_2$ represents a —$CH_2$-pyridinium compound, the carboxyl group in the general formula I is present as an inner salt (—$COO^{(-)}$).

As cephalosporin derivatives of particular interest, cefotiam from amongst the aminothiazole-cephalosporins which contain —$CH_2$— in place of —C(=N—$OR_1$)— and cefoperazon from amongst the N-acyl-phenylglycine-cephalosporins should also be mentioned.

Of the penem antibiotics of the basic structure B, those of the general formula II are particularly preferred

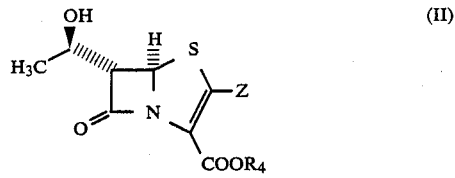

in which
Z can be

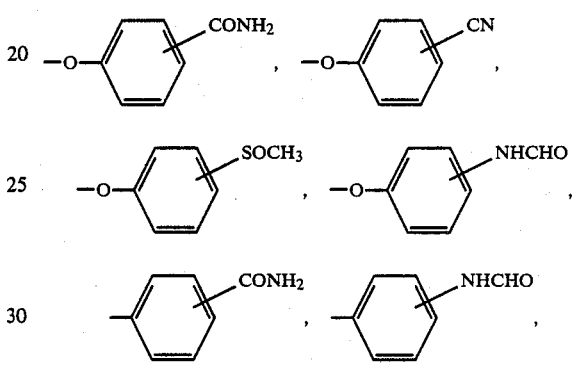

—S—$(CH_2)_2$—O—$CONH_2$ or —S—$(CH_2)_3$—$SO_2NH_2$ and $R_4$ is hydrogen, a physiologically acceptable cation or a physiologically acceptable ester radical. Of the substituted phenoxy and phenyl substituents listed above, the radicals

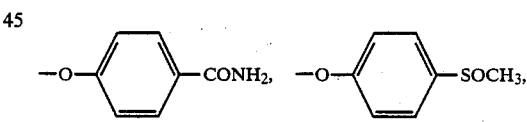

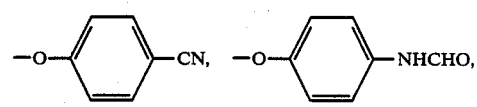

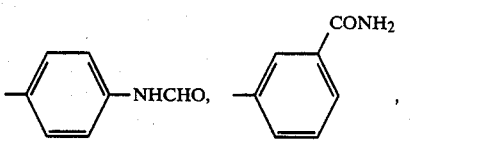

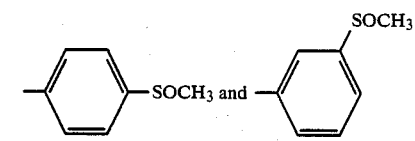

are preferred, and the 3-carbamoyl-phenoxy radical (HRE 664) is to be particularly singled out.

Accordingly, a combination of cefodizim or cefpirom, and especially of cefotaxim and the penem HRE 664, is of particular interest according to the invention.

$R_3$ and $R_4$ can be hydrogen or a physiologically acceptable cation such as, for example, an alkali metal cation, preferably potassium or sodium, in particular sodium, or also other physiologically acceptable salts, known from the literature, with alkaline earth metal ions or organic ammonium ions (cf., for example, U.S. Pat. No. 4,278,793).

Moreover, $R_3$ and $R_4$ can be a physiologically acceptable ester radical, of interest especially for enteral administration, such as, for example, an acyloxymethyl or acyloxyethyl radical having 2 to 12, preferably 2 to 6, carbon atoms in the acyl moiety, preferably acetoxymethyl, 1'-(acetoxy)ethyl or pivaloyloxymethyl, 5-methyl-1,3-dioxalen-2-on-4-yl-methyl, or also other physiologically acceptable esters such as are described, for example, in EP-A No. 0,170,028.

The preparation of the components, which can be used according to the invention, in the active compound combination is described by way of example in the patent rights quoted above.

The combination, according to the invention, of cephalosporins and penems has a strong antibacterial action and is therefore very particularly suitable for the treatment of bacterial infections. The essential fact is that the action of the two components does not show additive behavior but that, rather, an unexpected, strong synergistic effect appears.

Even in the case of pathogens, towards which one individual component alone does not have a significant antibacterial action, a synergistic effect can be observed in combination.

The formulations according to the invention thus cover a spectrum of pathogens at low minimum inhibitory concentrations, which are not reached by the individual components.

For the above reasons, the formulation according to the invention is superior to the individual components in the treatment of bacterial infections. It allows to administer lower dosages of the individual components and nevertheless to achieve a greater therapeutic effect.

The invention also relates to a process for the preparation of such a formulation, which comprises bringing (a) a cephalosporin derivative or physiologically acceptable salts or esters thereof and (b) a penem antibiotic of the basic structure (B) or physiologically acceptable salts or esters thereof together with (a) physiologically acceptable excipient(s) and, if appropriate, further auxiliaries or additives into a suitable administration form.

Moreover, the invention relates quite generally to pharmaceutical products which comprise side by side in an unmixed form (a) a cephalosporin derivative or physiologically acceptable salts or esters thereof and (b) a penem antibiotic of the basic structure (B) or physiologically acceptable salts or esters thereof as a combination product for simultaneous or separate application or for application spaced out in time in the treatment of bacterial infections.

The dosages of the cephalosporin derivative and of the penem antibiotic are preferably selected in the formulations according to the invention such that the individual components would not yet shown an adequate or full activity. The daily dose of the combinations according to the invention (sum of the individual components) is between about 1 to 16 g, preferably about 4 to 8 g. The ratio of the individual components in the combination can be between about 1:9 and 9:1, preferably between about 1:5 and 5:1. The dose in one administration unit can be chosen, for example, between about 50 and 2,000 mg.

Since the preparation of the cephalosporin component in general requires less effort and is therefore also less expensive than the preparation of the penem antibiotic, a combination according to the invention in which the cephalosporin proportion is higher than that of the penem will be preferable for this reason alone.

The formulations or products according to the invention can be administered parenterally or orally. Parenteral administration is preferred.

The active compound combinations according to the invention, which can be used in chemotherapy, can be used for the preparation of pharmaceutical products which contain an effective amount of the active substances together with excipients and which are suitable for enteral and parenteral administration. Injectable solutions are preferably isotonic aqueous solutions or suspensions, which may have been sterilized and can contain auxiliaries such as preservatives, stabilizers, wetting agents and/or emulsifiers, solubilizers, salts for regulating the osmotic pressure and/or buffer substances. The pharmaceutical products according to the invention which, if desired, can contain further chemotherapeutically valuable substances, are prepared, for example, by means of conventional processes.

For parenteral administration, the combination according to the invention is preferably dissolved, immediately before use, in sterile water or — if necessary — a buffer solution such as, for example, a phosphate or carbonate buffer such as is conventionally used for these purposes, and subsequently administered.

The examples which follow serve to explain the invention without restricting the latter thereto.

EXAMPLE 1

Action of the combination of the sodium salt of 5R,6S-6-(1R-hydroxyethyl)-3-(4-carbamoylphenoxy)-7-oxo-4-thia-1-azabicyclo[3.2.0]hept-2-ene-carboxylic acid (HRE 664, marked (1) in the Table) and of the sodium salt of cefotaxim (2) towards Gram-positive and Gram-negative test strains. To determine the synergism, mixtures of compound (1) with compound (2) were prepared in a ratio of 1:1, 1:2 and 1:3. The MIC values were tested by comparison with the individual substances.

TABLE 1

| | MIC in mg/l | | | | |
|---|---|---|---|---|---|
| Pathogen | (1) alone | (2) alone | 1:1 | (1):(2) 1:2 | 1:3 |
| Staph. SG 511 | 0.062 | 2 | 0.125 | 0.125 | 0.125 |
| Staph. 285 | 0.062 | 2 | 0.125 | 0.125 | 0.125 |
| Staph. 503 | 0.062 | 2 | 0.125 | 0.125 | 0.125 |
| Kl. aerog. 1082E | 0.5 | 1 | 0.5 | 0.5 | 0.5 |
| Citrob. 82 Cull. | 1 | 2 | 0.5 | 0.5 | 0.25 |

EXAMPLE 2

Action of the combination of (1) and (2) towards clinical isolates resistant to the cephalosporin component.

TABLE 2

| Pathogen | MIC in mg/l | | | | |
|---|---|---|---|---|---|
| | (1) alone | (2) alone | 1:1 | (1):(2) 1:2 | 1:3 |
| Staph. 789 | 4 | 64 | 4 | 4 | 8 |
| Staph. 22130 | 2 | 32 | 4 | 4 | 4 |
| Strept. D 756 | 8 | 64 | 4 | 4 | 4 |
| Strept. D Eder | 8 | 64 | 4 | 4 | 4 |
| Strept. faecium D | 8 | 64 | 8 | 16 | 8 |
| Citrob. 2901 | 8 | 64 | 4 | 4 | 4 |
| Ent. cl. M 423 | 4 | 64 | 2 | 2 | 4 |
| Ent. cl. M. 447 | 16 | 64 | 16 | 8 | 8 |
| Ent. cl. P99 | 2 | 64 | 2 | 2 | 2 |

EXAMPLE 3

Action of the combination of (1) and (2) on anaerobic pathogens

TABLE 3

| Pathogen | MIC in mg/l | | | | |
|---|---|---|---|---|---|
| | (1) alone | (2) alone | 1:1 | (1):(2) 1:2 | 1:3 |
| B. fragilis 312 | 0.125 | 128 | 0.125 | 0.25 | 0.25 |
| B. fragilis 960 | 0.125 | 16 | 0.125 | 0.125 | 0.125 |
| B. fragilis 17390 | 0.25 | 8 | 0.25 | 0.5 | 0.25 |
| B. fragilis 18125 | 0.25 | 2 | 0.25 | 0.25 | 0.25 |
| B. ovatus 103 | 0.125 | 64 | 0.125 | 0.125 | 0.125 |
| B. vulgatus 1446 | 0.125 | 64 | 0.125 | 0.125 | 0.125 |
| B. thetaiotaomicron 123 | 0.125 | 64 | 0.125 | 0.125 | 0.125 |
| Sph. varius 5262 | 0.25 | 64 | 0.5 | 1 | 1 |
| Cl. tetani 19406 | 0.25 | 8 | 0.5 | 0.5 | 0.5 |

EXAMPLE 4

The combination of the potassium salt of the penem compound 5R,6S-3-(2-carbamoyloxy-ethylthio)-6-(1R-hydroxyethyl)-7-oxo-4-thia-1-azabicyclo[3.2.0]hept-2-ene-carboxylic acid (3) with compound (2) was tested on 3 strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

TABLE 4

| Strain | FIC values of a combination of the penem (3) with the cephalosporin (2) |
|---|---|
| E. coli 2136E | 0.5 |
| E. coli 2137E | 0.75* |
| E. coli 2138E | 0.5 |
| Citrobacter freundii 8090 | 0.281 |

*The FIC value of 0.75 indicates a hyperadditive action.

EXAMPLE 5

The combination of the potassium salt of the penem compound 5R,6S-6-(1R-hydroxyethyl)-3-(4-formamidophenyl)-7-oxo-4-thia-1-azabicyclo[3.2.0]hept-2-ene-2-carboxylic acid (4) with compound (2) was tested on 3 strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

TABLE 5

| Strain | FIC values of a combination of the penem (4) with the cephalosporin (2) |
|---|---|
| E. coli 2136E | 0.5 |
| E. coli 2137E | 0.375 |
| E. coli 2138E | 0.5 |
| Citrobacter freundii 8090 | 0.091 |

EXAMPLE 6

The combination of the sodium salt of the penem compound 5R,6S-3-(3-carbamoylphenyl)-6-(1R-hydroxyethyl)-7-oxo-4-thia-1-azabicyclo[3.2.0]hept-2-ene-2-carboxylic acid (5) with compound (2) was tested on 3 strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

TABLE 6

| Strain | FIC values of a combination of the penem (5) with the cephalosporin (2) |
|---|---|
| E. coli 2136E | 0.375 |
| E. coli 2137E | 0.5 |
| E. coli 2138E | 0.375 |
| Citrobacter freundii 8090 | 0.125 |

EXAMPLE 7

The activity of cephalosporins, such as are indicated above as an example, towards Gram-positive pathogens such as staphylococci and towards Gram-negative anaerobic pathogens is in most cases lower than that towards Gram-negative aerobic pathogenic organisms (see also Seibert et al., Infection, Volume 11 (1983) 5, 275–279).

By contrast, penems have as a rule a higher antibacterial activity towards Gram-positive cocci and anaerobics than towards Gram-negative pathogens (see also Bauernfeind, J. Antimicrob. Chemother 15, 111, 1985).

Taking a combination of one part of a penem and three parts of a cephalosporin as an example, Table 7 shows a superiority of the antibacterial activity of the combination as compared with the individual components. The combination product evens out the weakness in the antibacterial spectrum of the two products and thus has a broader antibacterial spectrum which makes it particularly suitable for a therapy of bacterial infections without preceding isolation of the causative organism.

TABLE 7

| Strain | MIC in mg/l | | |
|---|---|---|---|
| | HRE 664 (1) | Cefotaxim (2) | (1):(2) 1:3 |
| Strept. D 756 | 8 | 64 | 4 |
| Strept. D Eder | 8 | 64 | 4 |
| Strept. D 21777 | 8 | 64 | 4 |
| Strept. D 26777 | 8 | 64 | 4 |
| Citrob. 2901 | 8 | 64 | 4 |
| Citrob. 82 Cull. | 1 | 2 | 0.25 |
| Ent. cl. M 447 | 16 | 64 | 8 |
| Ent. cl. 2240 Cull. | 2 | 0.062 | 0.015 |
| E. coli 2139E | 1 | 0.031 | 0.015 |
| Kl. pneu. 1976E | 1 | 0.062 | 0.031 |
| B. vulgatus 1446 | 0.125 | 64 | 0.125 |

TABLE 7-continued

| | MIC in mg/l | | |
|---|---|---|---|
| Strain | HRE 664 (1) | Cefotaxim (2) | (1):(2) 1:3 |
| B. distasonis 1366 | 0.25 | 0.125 | 0.125 |

EXAMPLE 8

The combination of sodium 5R,6S-6-(1R-hydroxyethyl)-3-(4-carbamoyl-phenoxy)-7-oxo-4-thia-1-azabicyclo[3.2.0]hept-2-ene-2-carboxylate (1) with cefotaxim was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.312 |
| E. coli 2137E | 0.312 |
| E. coli 2138E | 0.249 |
| Citrobacter freundii 8090 | 0.094 |

EXAMPLE 9

The combination of sodium 5R,6S-6-(1R-hydroxyethyl)-3-(4-methyl-sulfinylphenyl)-7-oxo-4-thia-1-azabicyclo[3.2.0]hept-2-ene-2-carboxylate (6) with cefotaxim (2) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC Index |
|---|---|
| E. coli 2136E | 0.379 |
| E. coli 2137E | 0.5 |
| E. coli 2138E | 0.282 |
| Citrobacter freundii 8090 | 0.5 |

EXAMPLE 10

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with cefotaxim (2) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.379 |
| E. coli 2137E | 0.320 |
| E. coli 2138E | 0.374 |
| Citrobacter freundii 8090 | 0.047 |

EXAMPLE 11

The combination of sodium 5R,6S-6-(1R-hydroxyethyl)-3-(3-sulfamoyl-propylthio)-7-oxo-4-thia-1-azabicyclo[3.2.0]hept-2-ene-2-carboxylate (8) with cefotaxim (2) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.379 |
| E. coli 2137E | 0.379 |
| E. coli 2138E | 0.379 |
| Citrobacter freundii 8090 | 0.312 |

EXAMPLE 12

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with cefotaxim (2) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.383 |
| E. coli 2137E | 0.383 |
| E. coli 2138E | 0.185 |
| Citrobacter freundii 8090 | 0.0935 |

EXAMPLE 13

The combination of sodium 5R,6S-3-(4-cyanophenoxy)-6-(1R-hydroxyethyl)-7-oxo-4-thia-1-azabicyclo[3.2.0]hept-2-ene-2-carboxylate (10) with cefotaxim (2) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.5 |
| E. coli 2137E | 0.25 |
| E. coli 2138E | 0.25 |
| Citrobacter freundii 8090 | 0.75 |

EXAMPLE 14

The combination of the sodium salt of 5R,6S-6-(1R-hydroxyethyl)-3-(4-carbamoyl-phenoxy)-7-oxo-4-thia-1-azobicyclo[3.2.0]hept-2-ene-carboxylic acid (1) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.49 |
| E. coli 2137E | 0.5 |
| E. coli 2138E | 0.37 |
| Citrobacter freundii | 0.186 |

EXAMPLE 15

The combination of sodium 5R,6S-6-(1R-hydroxyethyl)-3-(4-methyl-sulfinylphenyl)-7-oxo-4-thia-1-azabicyclo[3.2.0]hept-2-ene-2-carboxylate (6) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.155 |
| E. coli 2137E | 0.498 |
| E. coli 2138E | 0.374 |
| Citrobacter freundii 8090 | 0.375 |

EXAMPLE 16

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.249 |
| Citrobacter freundii 8090 | 0.140 |

EXAMPLE 17

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.125 |
| E. coli 2137E | 0.187 |
| E. coli 2138E | 0.375 |
| Citrobacter freundii 8090 | 0.093 |

EXAMPLE 18

The combination of sodium 5R,6S-3-(4-cyanophenoxy)-6-(1R-hydroxyethyl)-7-oxo-4-thia-1-azabicyclo[3.2.0]hept-2-ene-2-carboxylate (10) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.75 |
| E. coli 2137E | 0.373 |
| E. coli 2138E | 0.498 |
| Citrobacter freundii 8090 | 0.062 |

EXAMPLE 19

The combination of sodium 5R,6S-6-(1R-hydroxyethyl)-3-(3-sulfamoyl-propylthio)-7-oxo-4-thia-1-azabicyclo[3.2.0]hept-2-ene-2-carboxylate (8) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.498 |
| E. coli 2137E | 0.498 |
| E. coli 2138E | 0.624 |
| Citrobacter freundii 8090 | 0.281 |

EXAMPLE 20

The combination of sodium 5R,6S-3-(3-carbamoylphenyl)-6-(1R-hydroxyethyl)-7-oxo-4-thia-1-azabicyclo[3.2.0]hept-2-ene-2-carboxylate (5) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.75 |
| E. coli 2137E | 0.496 |
| E. coli 2138E | 1 |
| Citrobacter freundii 8090 | 0.187 |

EXAMPLE 21

The combination of sodium 5R,6S-6-(1R-hydroxyethyl)-3-(2-carbamoyl-oxyethlthio)-7-oxo-4-thia-1-azabicyclo[3.2.0]hept-2-ene-2-carboxylate (3) with cefodizim (11) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.498 |
| E. coli 2137E | 0.498 |
| E. coli 2138E | 0.5 |
| Citrobacter freundii 8090 | 0.249 |

EXAMPLE 22

The combination of potassium 5R,6S-6-(1R-hydroxyethyl)-3-(4-formamidophenyl)-7-oxo-4-thia-1-azabicyclo[3.2.0]hept-2-ene-2-carboxylate (4) with cefodizim (11) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.75 |
| E. coli 2138E | 0.5 |
| Citrobacter freundii 8090 | 0.125 |

EXAMPLE 23

The combination of the sodium salt of 5R,6S-6-(1R-hydroxyethyl)-3-(4-carbamoyl-phenoxy)-7-oxo-4-thia-1-azabicyclo[3.2.0]hept-2-ene-2-carboxylic acid (1) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.66 |
| E. coli 2138E | 0.315 |
| Citrobacter freundii | 0.5 |

EXAMPLE 24

The combination of sodium 5R,6S-6-(1R-hydroxyethyl)-3-(4-methylsulfinylphenyl)-7-oxo-4-thia-1-azabicyclo[3.2.0]hept-2-ene-2-carboxylate (6) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.374 |
| E. coli 2137E | 0.249 |
| E. coli 2138E | 0.187 |
| Citrobacter freundii 8090 | 0.126 |

EXAMPLE 25

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.629 |
| E. coli 2137E | 0.5 |
| E. coli 2138E | 0.5 |
| Citrobacter freundii 8090 | 0.126 |

EXAMPLE 26

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.125 |
| E. coli 2137E | 0.5 |
| E. coli 2138E | 0.186 |

-continued

| Strain | FIC index |
|---|---|
| Citrobacter freundii 8090 | 0.258 |

EXAMPLE 27

The combination of sodium 5R,6S-3-(4-cyanophenoxy)-6-(1R-hydroxyethyl)-7-oxo-4-thia-1-azabicyclo[3.2.0]hept-2-ene-2-carboxylate (10) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.5 |
| E. coli 2138E | 0.5 |
| Citrobacter freundii 8090 | 0.062* |

EXAMPLE 28

The combination of sodium 5R,6S-6-(1R-hydroxyethyl)-3-(3-sulfamoyl-propylthio)-7-oxo-4-thia-1-azabicyclo[3.2.0]hept-2-ene-2-carboxylate (8) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.75 |
| E. coli 2137E | 0.62 |
| E. coli 2138E | 0.5 |
| Citrobacter freundii 8090 | 0.5 |

EXAMPLE 29

The combination of sodium 5R,6S-3-(3-carbamoyl-phenyl)-6-(1R-hydroxyethyl)-7-oxo-4-thia-1-azabicyclo[3.2.0]hept-2-ene-2-carboxylate (5) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.75 |
| E. coli 2138E | 0.372 |
| Citrobacter freundii 8090 | 0.390 |

EXAMPLE 30

The combination of sodium 5R,6S-6-(1R-hydroxyethyl)-3-(2-carbamoyloxyethyl)-7-oxo-4-thia-1-azabicyclo[3.2.0]hept-2-ene-2-carboxylate (3) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.366 |
| E. coli 2137E | 0.496 |
| E. coli 2138E | 0.372 |
| Citrobacter freundii 8090 | 0.366 |

EXAMPLE 31

The combination of potassium 5R,6S-6-(1R-hydroxyethyl)-3-(4-formamidophenyl)-7-oxo-4-thia-1-azabicyclo[3.2.0]hept-2-ene-2-carboxylate (4) with cefpirome (12) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.5 |
| E. coli 2138E | 0.312 |
| Citrobacter freundii 8090 | 0.125 |

EXAMPLE 32

The combination of the sodium salt of 5R,6S-6-(1R-hydroxyethyl)-3-(4-carbamoyl-phenoxy)-7-oxo-4-thia-1-azabicyclo[3.2.0]hept-2-ene-2-carboxylic acid (1) with ceftriaxon (13) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
|---|---|
| E. coli 2136E | 0.5 |
| E. coli 2137E | 0.379 |
| E. coli 2138E | 0.75 |
| Citrobacter freundii 8090 | 0.075 |

EXAMPLE 33

The combination of sodium 5R,6S-6-(1R-hydroxyethyl)-3-(4-methylsulfinylphenyl)-7-oxo-4-thia-1-azabicyclo[3.2.0]hept-2-ene-2-carboxylate (6) with ceftriaxon (13) was tested on three strains of E. coli and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.498 |
| E. coli 2138E | 0.374 |
| Citrobacter freundii 8090 | 0.187 |

EXAMPLE 34

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.75 |
| Citrobacter freundii 8090 | 0.091 |

EXAMPLE 35

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.125 |
| E. coli 2137E | 0.75 |
| E. coli 2138E | 0.077 |
| Citrobacter freundii 8090 | 0.034 |

EXAMPLE 36

The combination of sodium 5R,6S-3-(4-cyanophenoxy)-6-(1R-hydroxyethyl)-7-oxo-4-thia-1-azabicyclo[3.2.0]-hept-2-ene-2-carboxylate (10) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.5 |
| Citrobacter freundii 8090 | 0.182 |

EXAMPLE 37

The combination of sodium 5R,6S-6-(1R-hydroxyethyl)-3-(3-sulfamoyl-propylthio)-7-oxo-4-thia-1-azabicyclo[3.2.0]hept-2-ene-2-carboxylate (8) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.5 |
| Citrobacter freundii 8090 | 0.186 |

EXAMPLE 38

The combination of sodium 5R,6S-3-(3-carbamoylphenyl)-6-(1R-hydroxyethyl)-7-oxo-4-thia-1-azabicyclo[3.2.0]hept-2-ene-2-carboxylate (5) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.318 |
| E. coli 2137E | 0.31 |
| E. coli 2138E | 0.75 |
| Citrobacter freundii 8090 | 0.06 |

EXAMPLE 39

The combination of sodium 5R,6S-6-(1R-hydroxyethyl)-3-(2-carbamoyloxyethylthio)-7-oxo-4-thia-1-azabicyclo[3.2.0]hept-2-ene-2-carboxylate (3) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.75 |

-continued

| Strain | FIC index |
|---|---|
| E. coli 2137E | 0.75 |
| E. coli 2138E | 0.629 |
| Citrobacter freundii | 0.0625 |

EXAMPLE 40

The combination of potassium 5R,6S-6-(1R-hydroxyethyl)-3-(4-formamidophenyl)-7-oxo-4-thia-1-azabicyclo[3.2.0]hept-2-ene-2-carboxylate (4) with ceftriaxon (13) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.5 |
| E. coli 2137E | 0.125 |
| E. coli 2138E | 0.5 |
| Citrobacter freundii 8090 | 0.372 |

EXAMPLE 41

The combination of the sodium salt of 5R,6S-6-(1R-hydroxyethyl)-3-(4-carbamoyl-phenoxy)-7-oxo-4-thia-1-azabicyclo[3.2.0]hept-2-ene-2-carboxylic acid (1) with cefotiam (14) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.49 |
| E. coli 2137E | 0.5 |
| E. coli 2138E | .0.372 |
| Citrobacter freundii | 0.077 |

EXAMPLE 42

The combination of sodium 5R,6S-6-(1R-hydroxyethyl)-3-(4-methylsulfinylphenyl)-7-oxo-4-thia-1-azabicyclo[3.2.0]hept-2-ene-2-carboxylate (6) with cefotiam (14) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.312 |
| E. coli 2137E | 0.375 |
| E. coli 2138E | 0.374 |

-continued

| Strain | FIC index |
|---|---|
| Citrobacter freudii 8090 | 0.312 |

EXAMPLE 43

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with cefotiam (14) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.498 |
| E. coli 2137E | 0.5 |
| E. coli 2138E | 0.374 |
| Citrobacter freundii 8090 | 0.077 |

EXAMPLE 44

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with cefotiam (14) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 0.75 |
| E. coli 2137E | 0.75 |
| E. coli 2138E | 0.5 |
| Citrobacter freundii 8090 | 0.125 |

EXAMPLE 45

The combination of sodium 5R,6S-3-(4-cyanophenoxy)-6-(1R-hydroxyethyl)-7-oxo-4-thia-1-azabicyclo[3.2.0]hept-2-ene-2-carboxylate (10) with cefotiam (14) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| E. coli 2136E | 1 |
| E. coli 2137E | 0.375 |
| E. coli 2138E | 0.375 |
| Citrobacter freundii 8090 | 0.186 |

EXAMPLE 46

The combination of sodium 5R,6S-6-(1R-hydroxyethyl)-3-(3-sulfamoylpropylthio)-7-oxo-4-thia-1-azabicyclo[3.2.0]hept-2-ene-2-carboxylate (8) with cefotiam (14) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.63 |
| *E. coli* 2137E | 0.75 |
| *E. coli* 2138E | 0.5 |
| *Citrobacter freundii* 8090 | 0.265 |

EXAMPLE 47

The combination of sodium 5R,6S-3-(3-carbamoylphenyl)-6-(1R-hydroxyethyl)-7-oxo-4-thia-1-azabicyclo[3.2.0]hept-2-ene-2-carboxylate (5) with cefotiam (14) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.75 |
| *E. coli* 2137E | 0.5 |
| *E. coli* 2138E | 0.5 |
| *Citrobacter freundii* 8090 | 0.186 |

EXAMPLE 48

The combination of sodium 5R,6S-6-(1R-hydroxyethyl)-3-(2-carbamoyloxyethio)-7-oxo-4-thia-1-azabicyclo[3.2.0]hept-2-ene-2-carboxylate (3) with cefotiam (14) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.5 |
| *E. coli* 2137E | 0.498 |
| *E. coli* 2138E | 0.498 |
| *Citrobacter freundii* 8090 | 0.124 |

EXAMPLE 49

The combination of potassium 5R,6S-6-(1R-hydroxyethyl)-3-(4-formamidophenyl)-7-oxo-4-thia-1-azabicyclo[3.2.0]hept-2-ene-2-carboxylate (4) with cefotiam (14) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.5 |
| *E. coli* 2137E | 0.5 |
| *E. coli* 2138E | 0.624 |
| *Citrobacter freundii* 8090 | 0.156 |

EXAMPLE 50

The combination of sodium 5R,6S-6-(1R-hydroxyethyl)-3-(4-carbamoyl-phenoxy)-7-oxo-4-thia-1-azabicyclo[3.2.0]hept-2-ene-2-carboxylate (1) with cefoperazon (15) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.5 |
| *E. coli* 2137E | 0.5 |
| *E. coli* 2138E | 0.278 |
| *Citrobacter freundii* 8090 | 0.09 |

EXAMPLE 51

The combination of sodium 5R,6S-6-(1R-hydroxyethyl)-3-(4-methylsulfinylphenyl)-7-oxo-4-thia-1-azabicyclo[3.2.0]hept-2-ene-2-carboxylate (6) with cefoperazon (15) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| *E. coli* 2136E | 0.25 |
| *E. coli* 2137E | 0.75 |
| *E. coli* 2138E | 0.498 |
| *Citrobacter freundii* 8090 | 0.056 |

EXAMPLE 52

The combination of sodium 5R,6S-3-(4-methylsulfinylphenoxy)-6-(1R-hydroxyethyl)-7-oxo-4-thia-1-azabicyclo[3.2.0]hept-2-ene-2-carboxylate (7) with cefoperazon (15) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.75 |
| E. coli 2137E | 0.75 |
| E. coli 2138E | 0.374 |
| Citrobacter freundii 8090 | 0.077 |

EXAMPLE 53

The combination of potassium 5R,6S-6-(1R-hydroxyethyl)-3-(3-methylsulfinylphenyl)-7-oxo-4-thia-1-azabicyclo[3.2.0]hept-2-ene-2-carboxylate (9) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.75 |
| Citrobacter freundii 8090 | 0.312 |

EXAMPLE 54

The combination of sodium 5R,6S-3-(4-cyanophenoxy)-6-(1R-hydroxyethyl)-7-oxo-4-thia-1-azabicyclo[3.2.0]hept-2-ene-2-carboxylate (10) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.5 |
| E. coli 2137E | 0.25 |
| E. coli 2138E | 0.28 |
| Citrobacter freundii 8090 | 0.091 |

EXAMPLE 55

The combination of sodium 5R,6S-6-(1R-hydroxyethyl)-3-(3-sulfamoyl-propylthio)-7-oxo-4-thia-1-azabicyclo[3.2.0]hept-2-ene-2-carboxylate (8) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.75 |
| E. coli 2137E | 0.75 |
| E. coli 2138E | 0.373 |
| Citrobacter freundii 8090 | 0.281 |

EXAMPLE 56

The combination of sodium 5R,6S-3-(3-carbamoylphenyl)-6-(1R-hydroxyethyl)-7-oxo-4-thia-1-azabicyclo[3.2.0]hept-2-ene-2-carboxylate (5) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.31 |
| E. coli 2137E | 0.374 |
| E. coli 2138E | 0.308 |
| Citrobacter freundii 8090 | 0.124 |

EXAMPLE 57

The combination of sodium 5R,6S-6-(1R-hydroxyethyl)-3-(2-carbamoyloxyethylthio)-7-oxo-4-thia-1-azabicyclo[3.2.0]hept-2-ene-2-carboxylate (3) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.563 |
| E. coli 2137E | 1 |
| E. coli 2138E | 0.5 |
| Citrobacter freundii 8090 | 0.366 |

EXAMPLE 58

The combination of potassium 5R,6S-6-(1R-hydroxyethyl)-3-(4-formamidophenyl)-7-oxo-4-thia-1-azabicyclo[3.2.0]hept-2-ene-2-carboxylate (4) with cefoperazon (15) was tested on three strains of E. coli and one strain of Citrobacter freundii. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
| --- | --- |
| E. coli 2136E | 0.75 |
| E. coli 2137E | 0.75 |
| E. coli 2138E | 0.372 |

-continued

| Strain | FIC index |
|---|---|
| *Citrobacter freundii* 8090 | 0.248 |

EXAMPLE 59

The combination of sodium 5R,6S-3-(4-formamidophenoxy)-6-(1R-hydroxyethyl)-7-oxo-4-thia-1-azabicyclo[3.2.0]hept-2-ene-2-carboxylate (16) with cefotaxim (2) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.383 |
| *E. coli* 2137E | 0.5 |
| *E. coli* 2138E | 0.374 |
| *Citrobacter freundii* 8090 | 0.122 |

EXAMPLE 60

The combination of sodium 5R,6S-3-(4-formamidophenoxy)-6-(1R-hydroxyethyl)-7-oxo-4-thia-1-azabicyclo[3.2.0]hept-2-ene-2-carboxylate (16) with cefodizim (11) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.5 |
| *E. coli* 2137E | 0.5 |
| *E. coli* 2138E | 0.125 |
| *Citrobacter freundii* 8090 | 0.047 |

EXAMPLE 61

The combination of sodium 5R,6S-3-(4-formamidophenoxy)-6-(1R-hydroxyethyl)-7-oxo-4-thia-1-azabicyclo[3.2.0]hept-2-ene-2-carboxylate (16) with cefpirome (12) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.5 |
| *E. coli* 2137E | 0.5 |
| *E. coli* 2138E | 0.5 |
| *Citrobacter freundii* 8090 | 0.273 |

EXAMPLE 62

The combination of sodium 5R,6S-3-(4-formamidophenoxy)-6-(1R-hydroxyethyl)-7-oxo-4-thia-1-azabicyclo[3.2.0]hept-2-ene-2-carboxylate (16) with ceftriaxon (13) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.5 |
| *E. coli* 2137E | 0.5 |
| *E. coli* 2138E | 0.36 |
| *Citrobacter freundii* 8090 | 0.122 |

EXAMPLE 63

The combination of sodium 5R,6S-3-(4-formamidophenoxy)-6-(1R-hydroxyethyl)-7-oxo-4-thia-1-azabicyclo[3.2.0]hept-2-ene-2-carboxylate (16) with cefotiam (14) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.5 |
| *E. coli* 2137E | 0.374 |
| *E. coli* 2138E | 0.374 |
| *Citrobacter freundii* 8090 | 0.257 |

EXAMPLE 64

The combination of sodium 5R,6S-4-(4-formamidophenoxy)-6-(1R-hydroxyethyl)-7-oxo-4-thia-1-azabicyclo[3.2.0]hept-2-ene-2-carboxylate (16) with cefoperazon (15) was tested on three strains of *E. coli* and one strain of *Citrobacter freundii*. The "fractional inhibitory concentration" (FIC index) as a measure of the synergistic activity was determined by the method of Berenbaum, J. Infect. Dis. 137 (1978), 122–136. According to this publication, FIC values of $\leq 0.5$ are characteristic of a synergistic activity, and FIC values of 1 show an additive interaction.

| Strain | FIC index |
|---|---|
| *E. coli* 2136E | 0.5 |
| *E. coli* 2137E | 0.75 |
| *E. coli* 2138E | 0.5 |
| *Citrobacter freundii* 8090 | 0.093 |

EXAMPLE 65

The combination of sodium 5R,6S-3-(carbamoyloxymethyl)-6-(1R-hydroxyethyl)-7-oxo-4-thia-1-azabicyclo[3.2.0]hept-2-ene-2-carboxylate (17) with cefotaxim (2) was tested on three strains of *E. coli* and one strain of

*Citrobacter freundii.* The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.37 |
| E. coli 2138E | 0.5 |
| Citrobacter freundii 8090 | 0.122 |

EXAMPLE 66

The combination of sodium 5R,6S-3-(carbamoyloxymethyl)-6-(1R-hydroxyethyl)-7-oxo-4-thia-1-azabicyclo[3.2.0]hept-2-ene-2-carboxylate (17) with cefodizim (11) was tested on three strains of *E. coli* and one strain of *Citrobacter freundii.* The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.5 |
| E. coli 2137E | 0.5 |
| E. coli 2138E | 0.75 |
| Citrobacter freundii 8090 | 0.125 |

EXAMPLE 67

The combination of sodium 5R,6S-3-(carbamoyloxymethyl)-6-(1R-hydroxyethyl)-7-oxo-4-thia-1-azabicyclo[3.2.0]hept-2-ene-2-carboxylate (17) with cefpirome (12) was tested on three strains of *E. coli* and one strain of *Citrobacter freundii.* The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.37 |
| E. coli 2137E | 0.5 |
| E. coli 2138E | 0.5 |
| Citrobacter freundii 8090 | 0.062 |

EXAMPLE 68

The combination of sodium 5R,6S-3-(carbamoyloxymethyl)-6-(1R-hydroxyethyl)-7-oxo-4-thia-1-azabicyclo[3.2.0]hept-2-ene-2-carboxylate (17) with ceftriaxon (13) was tested on three strains of *E. coli* and one strain of *Citrobacter freundii.* The "fractional inhibitory concentration" (FIC index) as a measure of the synergistic activity was determined by the method of Berenbaum, J. Infect. Dis. 137 (1978), 122–136. According to this publication, FIC values of ≦0.5 are characteristic of a synergistic activity, and FIC values of 1 show an additive interaction.

| Strain | FIC index |
| --- | --- |
| E. coli 2136E | 0.375 |
| E. coli 2137E | 0.125 |
| E. coli 2138E | 0.5 |
| Citrobacter freundii 8090 | 0.093 |

EXAMPLE 69

Preparation of a parenteral formulation 1.5 g of cefotaxim (2) and 0.5 g of HRE 664 (1) are dissolved in 10 ml of water ad injec. and then administered.

Depending on the solubility properties, similar quantity ratios are also applicable to the other illustrative examples described above.

Compounds of the illustrative examples

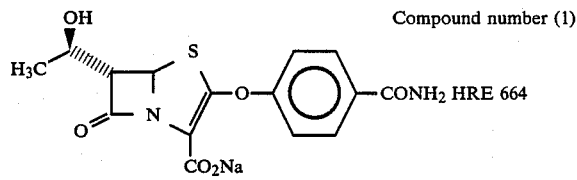

5R,6S-6-(1R-Hydroxyethyl)-3-(4-carbamoyl-phenoxy)-7-oxo-4-thia-1-azabicyclo[3.2.0]hept-2-ene-2-carboxylic acid (sodium salt)

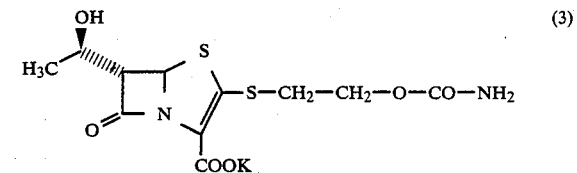

5R,6S-3-(2-Carbamoyloxyethylthio)-6-(1R-hydroxyethyl)-7-oxo-4-thia-1-azabicyclo[3.2.0]hept-2-ene-2-carboxylic acid (potassium salt)

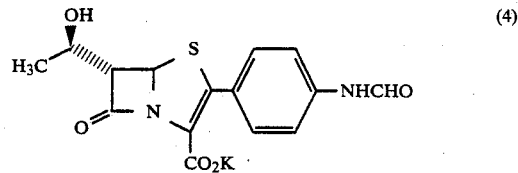

5R,6S-6-(1R-Hydroxyethyl)-3-(4-formamidophenyl)-7-oxo-4-thia-1-azabicyclo[3.2.0]hept-2-ene-2-carboxylic acid (potassium salt)

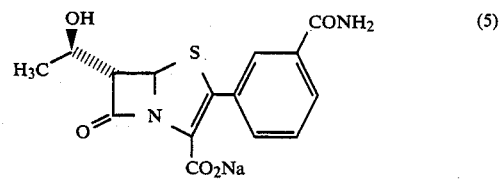

5R,6S-3-(3-Carbamoyl-phenyl)-6-(1R-hydroxyethyl)-7-oxo-4-thia-1-azabicyclo[3.2.0]hept-2-ene-2-carboxylic acid (sodium salt)

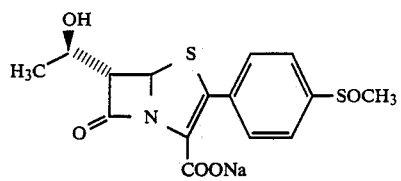
(6)

5R,6S-6-(1R-Hydroxyethyl)-3-(3-sulfamoyl-propylthio)-7-oxo-4-thia-1-azabicyclo[3.2.0]hept-2-ene-2-carboxylic acid (sodium salt)

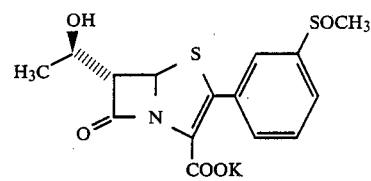
(9)

5R,6S-6-(1R-Hydroxyethyl)-3-(4-methylsulfinyl-phenyl)-7-oxo-4-thia-1-azabicyclo[3.2.0]hept-2-ene-2-carboxylic acid (sodium salt)

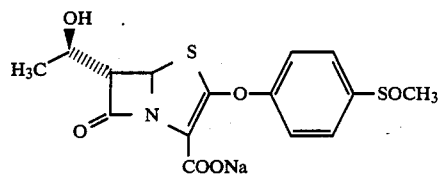
(7)

5R,6S-6-(1R-Hydroxyethyl)-3-(3-methylsulfinyl-phenyl)-7-oxo-4-thia-1-azabicyclo[3.2.0]hept-2-ene-2-carboxylic acid (potassium salt)

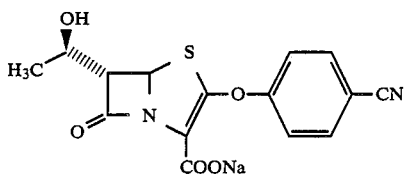
(10)

5R,6S-3-(4-Methylsulfinyl-phenoxy)-6-(1R-hydroxyethyl)-7-oxo-4-thia-1-azabicyclo[3.2.0]hept-2-ene-2-carboxylic acid (sodium salt)

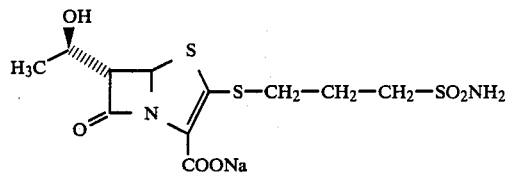
(8)

5R,6S-3-(4-Cyanophenoxy)-6-(1R-hydroxyethyl)-7-oxo-4-thia-1-azabicyclo[3.2.0]hept-2-ene-2-carboxylic acid (sodium salt)

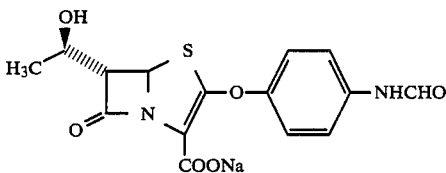
(16)

5R,6S-3-(4-Formamido-phenoxy)-6-(1R-hydroxyethyl)-7-oxo-4-thia-1-azabicyclo[3.2.0]hept-2-ene-2-carboxylic acid (sodium salt)

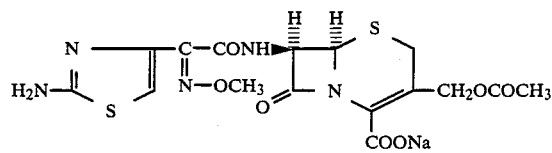
(2)

Cefotaxim (sodium salt)

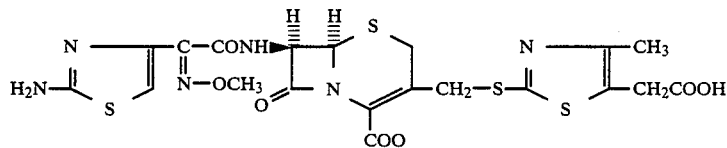
(11)

Cefodizim (sodium salt)

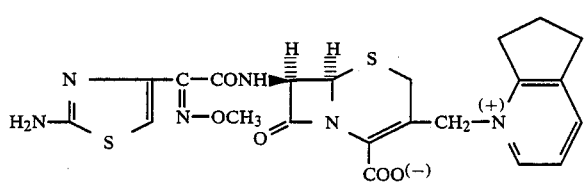
(12)

Cefpirom

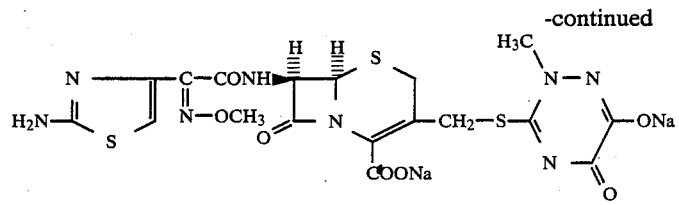

Ceftriaxon (disodium salt)

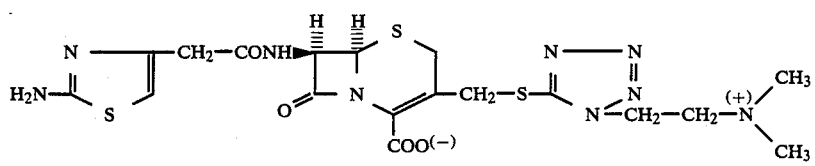

Cefotiam

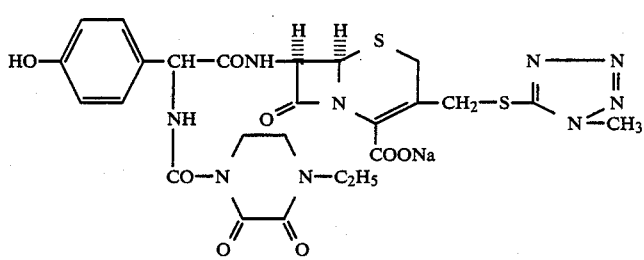

Cefoperazon (sodium salt)

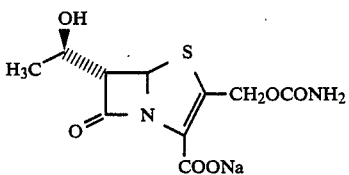

5R,6S-3-(Carbamoyloxymethyl)-6-(1R-hydroxyethyl)-7-oxo-4-thia-1-azabicyclo[3.2.0]hept-2-ene-2-carboxylic acid (sodium salt)

What is claimed is:

1. A pharmaceutical formulation having a synergistic antibacterial activity, comprising
   (a) a cephalosporin derivative of the formula I

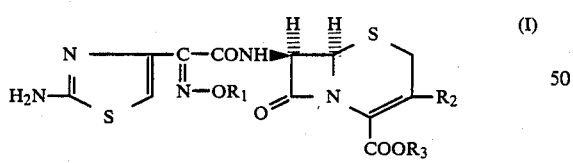

in which
$R_1$ can be $C_1$-$C_4$-alkyl and the $=N-OR_1$ group is in the synposition,
$R_2$ can have the meaning of acetoxymethyl, of $-CH_2S-X$,
with x=

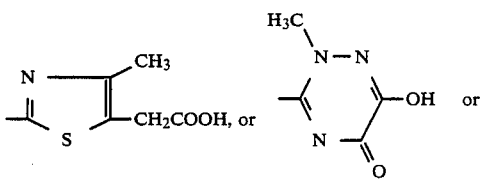

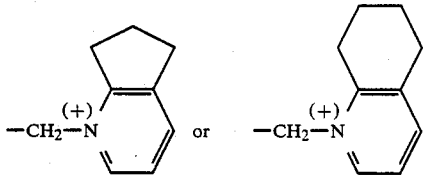

and
$R_3$ is hydrogen, a physiologically acceptable cation, a physiologically acceptable ester radical or, if the structure $-CH_2-(^+)$ appears in $R_2$, can represent a negative charge, or (b) a cephalosporin derivative of the formula

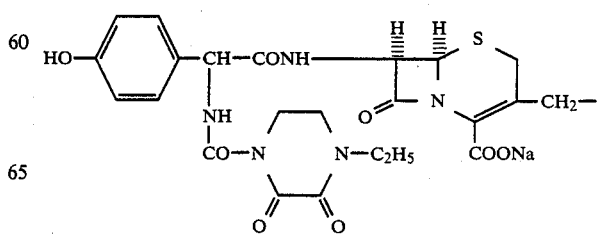

or (c) a cephalosporin derivative of the formula

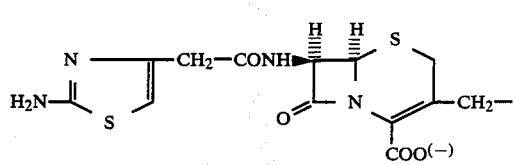

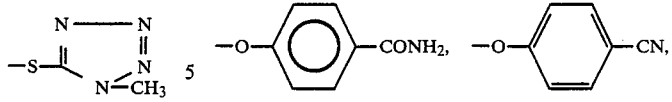

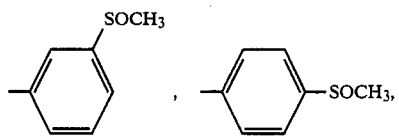

and (d) a penem antibiotic of the formula II

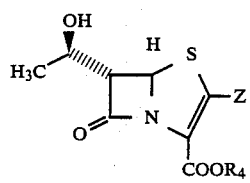   II in which Z can be

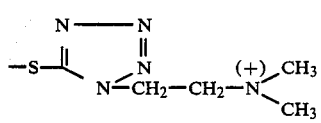

—CH₂—O—CONH₂, —S—(CH₂)₂—O—CONH₂ or —S—(CH₂)₃—SO₂NH₂ and $R_4$ can be a physiologically acceptable cation or a physiologically acceptable ester radical, and wherein the ratio of cephalosporin to penem antibiotic is between 1:9 and 9:1.

2. A method of treating bacterial infections in humans and animals wherein a cephalosporin derivative as defined in claim 1 is administered together with a penem antibiotic of formula II as defined in claim 1 and pharmaceutically acceptable excipients suitable for parenteral or enteral administration, in a daily dose of about 1 to 16 grams in which the individual components are combined in a ratio between 1:9 and 9:1.

* * * * *